(12) United States Patent
Ray et al.

(10) Patent No.: US 6,602,291 B1
(45) Date of Patent: Aug. 5, 2003

(54) PROSTHETIC SPINAL DISC NUCLEUS HAVING A SHAPE CHANGE CHARACTERISTIC

(75) Inventors: Charles D. Ray, Williamsburg, VA (US); Robert L. Assell, Mendota Heights, MN (US)

(73) Assignee: Raymedica, Inc., Bloomington, MN (US)

( * ) Notice: Subject to any disclaimer, the term of this patent is extended or adjusted under 35 U.S.C. 154(b) by 137 days.

(21) Appl. No.: 09/286,047

(22) Filed: Apr. 5, 1999

(51) Int. Cl.⁷ .................................................. A61F 2/44
(52) U.S. Cl. .................................. 623/17.11; 623/16.11
(58) Field of Search ...................................... 623/16, 17

(56) References Cited

U.S. PATENT DOCUMENTS

| | | | |
|---|---|---|---|
| 3,875,595 A | 4/1975 | Froning | 3/1 |
| 4,349,921 A | 9/1982 | Kuntz | 3/1 |
| 4,772,287 A | 9/1988 | Ray et al. | 623/17 |
| 4,863,477 A | 9/1989 | Monson | 623/17 |
| 4,904,260 A | 2/1990 | Ray et al. | 623/17 |
| 4,911,718 A | 3/1990 | Lee et al. | 623/17 |
| 4,932,969 A * | 6/1990 | Frey et al. | 623/17 |
| 5,047,055 A * | 9/1991 | Bao et al. | 623/17 |
| 5,071,437 A * | 12/1991 | Steffee | 623/17 |
| 5,123,926 A | 6/1992 | Pisharodi | 623/17 |
| 5,171,280 A | 12/1992 | Baumgartner | 623/17 |
| 5,192,326 A | 3/1993 | Bao et al. | 623/17 |
| 5,306,308 A | 4/1994 | Gross et al. | 623/17 |
| 5,306,309 A | 4/1994 | Wagner et al. | 623/17 |
| 5,401,269 A | 3/1995 | Büttner-Janz et al. | 623/17 |
| 5,458,642 A | 10/1995 | Beer et al. | 623/17 |
| 5,458,643 A * | 10/1995 | Oka et al. | 623/18 |
| 5,514,180 A | 5/1996 | Heggeness et al. | 623/17 |
| 5,534,028 A * | 7/1996 | Bao et al. | 623/17 |
| 5,545,229 A | 8/1996 | Parsons et al. | 623/17 |
| 5,571,189 A | 11/1996 | Kuslich | 623/17 |
| 5,609,636 A | 3/1997 | Kohrs et al. | 623/17 |
| 5,645,597 A | 7/1997 | Krapiva | 623/17 |
| 5,653,761 A | 8/1997 | Pisharodi | 623/17 |
| 5,653,762 A | 8/1997 | Pisharodi | 623/17 |
| 5,674,295 A | 10/1997 | Ray et al. | 623/17 |
| 5,674,296 A | 10/1997 | Bryan et al. | 623/17 |
| 5,676,701 A | 10/1997 | Yuan et al. | 623/17 |
| 5,676,702 A | 10/1997 | Ratron | 623/17 |
| 5,702,450 A * | 12/1997 | Bisserie | 623/17 |
| 5,705,780 A | 1/1998 | Bao | 204/157.15 |
| 5,766,252 A | 6/1998 | Henry et al. | 623/17 |
| 5,800,549 A | 9/1998 | Bao et al. | 623/17 |
| 5,824,093 A * | 10/1998 | Ray et al. | 623/17 |
| 5,824,094 A | 10/1998 | Serhan et al. | 623/17 |
| 5,865,846 A * | 2/1999 | Bryan et al. | 623/17 |
| 6,022,376 A * | 2/2000 | Assell et al. | 623/17 |

FOREIGN PATENT DOCUMENTS

FR   2 639 823 A1   6/1990   ............. A61F/2/44

OTHER PUBLICATIONS

Article entitled, *The Artificial Disc Introduction, History and Socioeconomics*, by Charles Dean Ray; p. 205–225; dated 1992.

* cited by examiner

*Primary Examiner*—Kevin Shaver
*Assistant Examiner*—Michael B. Priddy
(74) *Attorney, Agent, or Firm*—Dicke, Billig & Czaja, PLLC

(57) ABSTRACT

A prosthetic spinal disc nucleus comprising a hydrogel core surrounded by a constraining jacket. The hydrogel core is configured to expand from a dehydrated state to a hydrated state. In the dehydrated state, the hydrogel core has a shape selected to facilitate implantation through an anulus opening. Further, in the hydrated state, the hydrogel core has a shape corresponding generally to a portion of a nucleus cavity, the hydrated shape being different from the dehydrated shape. Upon hydration, the hydrogel core transitions from the dehydrated shape to the hydrated shape.

20 Claims, 6 Drawing Sheets

PROSTHETIC SPINAL DISC NUCLEUS HAVING A SHAPE CHANGE CHARACTERISTIC

BACKGROUND OF THE INVENTION

The present invention relates to a prosthetic spinal disc nucleus. More particularly, it relates to a prosthetic spinal disc nucleus having a pre-implant shape for facilitating implantation and a different, post-implant shape for restoring proper spacing and anatomical configuration of an intradiscal space.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, with a neural (vertebral) arch that arises from a posterior surface of the vertebral body. Each narrow arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The central portions of adjacent vertebrae are each supported by an intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the opposing vertebral bodies. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into, and released from, the nucleus by cyclic loading. When fluid is forced out of the nucleus, it passes again through the end plates and then back into the richly vascular vertebral bodies. The cyclic loading amounts to daily variations in applied pressure on the vertebral column (e.g., body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the resulting tightening and loosening effect on the anulus stimulates the normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal loading cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

The first prostheses embodied a wide variety of ideas, such as ball bearings, springs, metal spikes and other perceived aids. These prosthetic discs were designed to replace the entire intervertebral disc space and were large and rigid. Beyond the questionable efficacy of those devices was the inherent difficulties encountered during implantation. Due to their size and inflexibility, these first generation devices required an anterior implantation approach as the barriers presented by the lamina and, more importantly, the spinal cord and nerve rootlets during posterior implantation, could not be avoided. Recently, smaller and more flexible prosthetic nucleus devices have been developed. With the reduction in prosthesis size, the ability to work around the spinal cord and nerve rootlets during posterior implantation has become possible.

Generally speaking, these reduced size prostheses are intended to serve as a replacement for the natural nucleus. In other words, the anulus and end plates remain intact, and the prosthesis implanted within the nucleus cavity. It is generally believed that this approach facilitates healing of the anulus. Unfortunately, however, inherent design characteristics of these prostheses may in fact damage the anulus. For example, Bao et al., U.S. Pat. No. 5,047,055, discloses a prosthetic nucleus made of a hydrogel material that is implanted into the intradiscal space in a dehydrated state. Following implant, the hydrogel material hydrates and expands without constraint to, at least in theory, a shape conforming to the natural nucleus. Similarly, Bao et al., U.S. Pat. No. 5,192,326, describes a prosthetic nucleus comprised of a solid hydrogel core or of a multiplicity of hydrogel beads surrounded by a membrane. Once again, this prosthesis is implanted into the disc space in a dehydrated state, subsequently hydrating, at least in theory, to a shape conforming to the natural nucleus. The prostheses of Bao, as well as other similar products, rely solely upon the natural anulus to constrain expansion of the hydrogel core. Obviously, this essentially uncontrolled expansion imparts a lateral force directly upon the anulus. In most situations, the anulus is already damaged, and any additional forces placed on the anulus by the prosthesis may impede healing and even cause further deterioration. Further, it is virtually impossible to accurately orientate the dehydrated prostheses of Bao within the nucleus cavity due to the confined environment.

As previously described, an important feature of a prosthetic nucleus is that the anulus is not entirely removed upon implantation. Normally, however, an opening of some type must be created through the anulus. The prosthetic nucleus is then passed through this opening for implantation into the nucleus cavity. Because creation of this opening traumatizes the anulus, it is highly desirable to minimize its size. Unfortunately, however, most prosthetic nucleus devices currently available do not account for this generally accepted implantation technique. For example, a relatively rigid prosthesis configured to approximate a shape of the natural nucleus requires an extremely large opening in the anulus in order for the prosthetic device to "pass" into the nucleus cavity. Further, a hydrogel-based prosthesis, such as that described in Bao, minimizes, at least in part, the size of the anulus opening in that the hydrogel prosthesis is implanted in a dehydrated state, thereby having a reduced overall size. However, even in the dehydrated state, the Bao prosthesis still has a shape generally conforming to that of a natural nucleus. As a result, regardless of orientation, a relatively blunt surface is presented to the anulus when attempting to implant. This blunt surface is not conducive to insertion through the anulus opening. In fact, the blunt surface may impede implantation, thereby requiring an enlarged opening in the anulus.

In addition to the above-described concern for minimizing stress on the anulus, anatomical variations of the nucleus cavity should also be considered. Generally speaking, each intradiscal space has a greater transverse diameter (as defined by the anulus) at a posterior side than at an anterior side. Additionally, the intradiscal space varies in height (as defined by the opposing end plates) from posterior side to anterior side. In this regard, each intradiscal space has a relatively unique height configuration. For example, the L3-L4 intradiscal space has a slightly greater height at a central area in comparison to the posterior and anterior sides. The L4-L5 intradiscal space displays a more dramatic increase in central height. Finally, the L5-S1 intradiscal space increases in height from the posterior side to the anterior side. Effectively, each intradiscal space can be generally referred to as having an anterior area. With these dimensional variations in mind, a "standard" or single-sized prosthesis likely will not meet the anatomical needs of each and every intradiscal space. This is especially true for a single, rigid prosthesis design sized to encompass the entire intradiscal space that therefore does not recognize the general distinction between the anterior area and the posterior area. A prosthetic nucleus that fails to account for the anatomical variation in height of the nucleus cavity may also result in an uneven load distribution across the prosthesis and therefore poor spacing performance.

Finally, restoring the nutrition-flushing cycle of a natural disc is important for a prosthetic spinal disc nucleus to be successful. As previously described, most of the nutrition for the inner anulus and nucleus is provided by diffusion through the end plates of the vertebral bodies and by the important pumping action between the partially loaded and fully loaded conditions of the disc. If the nutritional cycle is impeded, a variety of degenerative changes may occur. Nutrition to the inner disc slowly ceases, resulting in intradiscal build-up of acids and autotoxins, and other changes. This is followed by anular fiber and nucleus degeneration, shrinkage of the nucleus, segmental laxity, spur formation, disc space collapse and perhaps spontaneous fusion. Significantly disabling back pain may also develop. Thus, a prosthetic nucleus sized to encompass the entire nucleus cavity prevents the fluid pumping action of the disc space from occurring, and will not result in complete healing.

Degenerated, painfully disabling intraspinal discs are a major economic and social problem for patients, their families, employers and the public at large. Any significant means to correct these conditions without further destruction or fusion of the disc may therefore serve an important role. Other means to replace the function of a degenerated disc have major problems such as complex surgical procedures, unproven efficacy, placing unnecessary and possibly destructive forces on an already damaged anulus, etc. Therefore, a substantial need exists for a prosthetic spinal disc nucleus formed to facilitate implantation through an anulus opening while providing necessary intradiscal support following implant.

SUMMARY OF THE INVENTION

The present invention provides an elongated prosthetic spinal disc nucleus for implantation within a nucleus cavity defined by opposing end plates and an anulus, and a method of manufacturing such a prosthesis. In one preferred embodiment, the prosthesis is comprised of a formed hydrogel core surrounded by a constraining jacket.

The hydrogel core is configured to expand from a dehydrated state to a hydrated state. In this regard, the hydrogel core has a dehydrated shape in the dehydrated state and a hydrated shape in the hydrated state. The dehydrated shape is configured to facilitate insertion of the prosthetic spinal disc nucleus through an opening in the anulus. Further, the dehydrated shape is generally different from the hydrated shape, which in one preferred embodiment relates to size characteristics of the nucleus cavity.

The constraining jacket surrounds the hydrogel core and constrains expansion upon hydration. The constraining jacket is preferably flexible but substantially inelastic. Further, in one preferred embodiment, the constraining jacket has a generally fixed maximum volume that is less than the volume of the nucleus cavity.

The method of manufacturing a prosthetic spinal disc nucleus in accordance with the present invention includes providing a hydrogel material that expands from a dehydrated state to a hydrated state. The hydrogel material is then formed into a hydrogel core having a first shape in the hydrated state. The hydrogel core is inserted into a constraining jacket and reshaped to have a second shape in the dehydrated state, the second shape being different from the first shape. In this regard, the hydrogel core is configured to transition from the second shape to the first shape upon hydration. In one preferred embodiment, reshaping the hydrogel core to have a second shape in the dehydrated state includes forcing the hydrogel core to an elongated shape defined by a leading end, a trailing end and a central portion, the hydrogel core tapering from the central portion to the leading end. This taper facilitates insertion of the leading end of the hydrogel core, otherwise encompassed by the constraining jacket, through an opening in the anulus.

The prosthetic spinal disc nucleus is implanted into the nucleus cavity with the hydrogel core in a dehydrated state. In one preferred embodiment, in the dehydrated state, the hydrogel core has a tapered leading end to facilitate insertion through an opening in the anulus. Once inserted, the prosthetic spinal disc nucleus is preferably transversely orientated within the nucleus cavity, and the hydrogel core is allowed to hydrate. During hydration, the hydrogel core transitions from the dehydrated shape to a predetermined hydrated shape. The hydrated shape preferably conforms with a general anatomical spacing of the particular disc space. For example, in one preferred embodiment, the hydrogel core is wedge shaped in the hydrated state, having a variable height corresponding generally to a shape of the nucleus cavity.

Another aspect of the present invention relates to a prosthetic spinal disc nucleus for implantation into a nucleus cavity of a spinal disc. The nucleus cavity has a height defined by an opposing pair of end plates and an outer periphery defined by an anulus. The prosthetic spinal disc nucleus comprises a formed hydrogel core surrounded by a constraining jacket. The formed hydrogel core is configured to expand from a dehydrated state to a hydrated state. The hydrogel core has a streamlined shape in the dehydrated state and a generally wedge shape in the hydrated state. Further, the hydrogel core is configured to transition from the streamlined shape to the wedge shape upon hydration. The constraining jacket is flexible but substantially inelastic, having a generally fixed maximum volume that is less than a volume of the nucleus cavity. With this configuration, the constraining jacket allows the hydrogel core to transition from the streamlined shape to the wedge shape upon hydration. However, the constraining jacket limits expansion of the hydrogel core in the hydrated state.

DESCRIPTION OF THE PREFERRED EMBODIMENTS

Figure 1A:
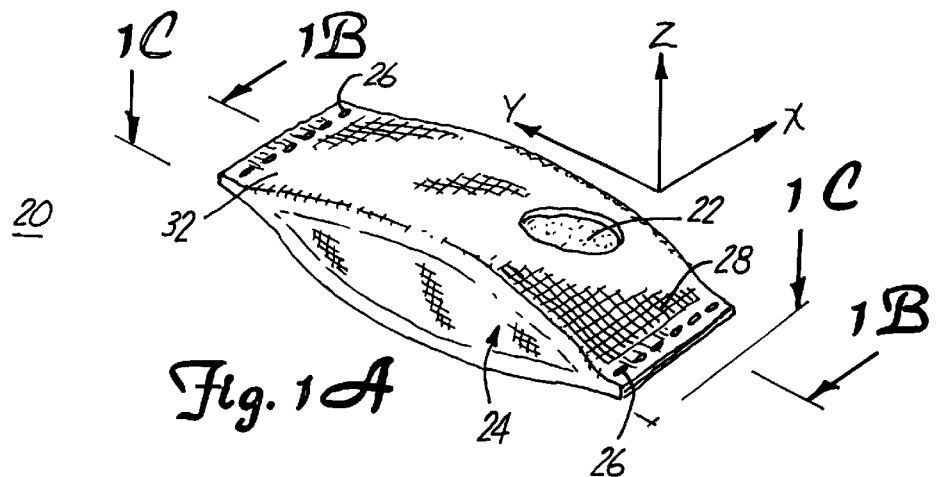
FIG. 1A is a perspective view of a prosthetic spinal disc nucleus in a dehydrated state, including a cutaway view showing a portion of a hydrogel core, in accordance with the present invention.

One preferred embodiment of a prosthetic spinal disc nucleus 20 is shown in FIG. 1A. The prosthetic spinal disc nucleus 20 is comprised of a hydrogel core 22 and a constraining jacket 24. The constraining jacket 24 is secured about the hydrogel core 22 by closures 26 located at opposite ends of the constraining jacket 24.

As will be made more clear below, the prosthetic spinal disc nucleus 20 of the present invention is described with reference to a first, pre-implant shape and a second, post-implant shape. To this end, because the hydrogel core 22 is dehydrated prior to implant and hydrated following implant, the pre-implant shape can also be referred to as a dehydrated shape; whereas the post-implant shape is referred to as a hydrated shape. As a point of reference, FIGS. 1A–1C depict the dehydrated shape; whereas FIG. 1D depicts the hydrated shape.

Figure 1B:
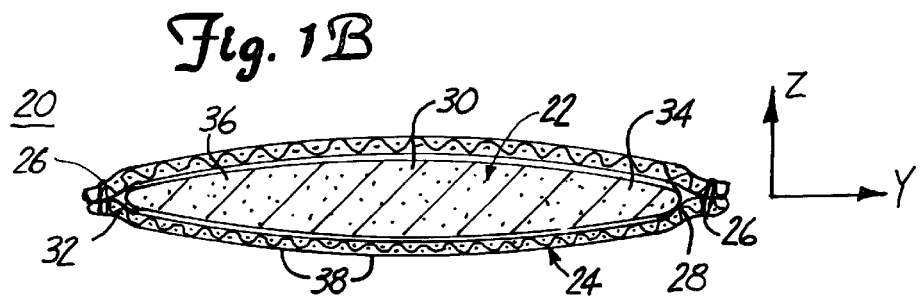
FIG. 1B is a side, sectional view of the prosthetic spinal disc nucleus of FIG. 1A along the line 1B—1B.
Figure 1C:
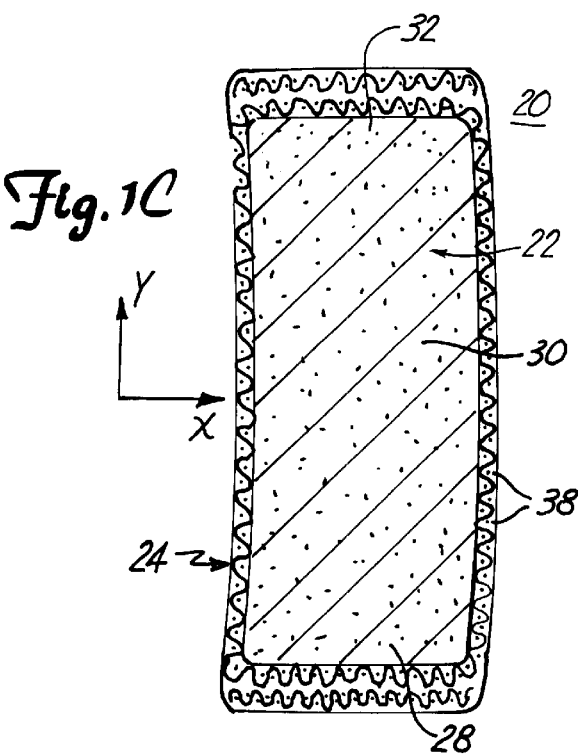
FIG. 1C is a top, sectional view of the prosthetic spinal disc nucleus of FIG. 1A along the line 1C—1C.
Figure 1D:
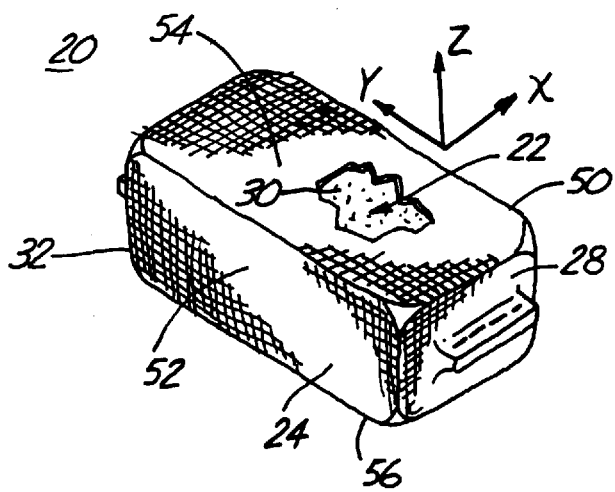
FIG. 1D is a perspective view of the prosthetic spinal disc nucleus of FIG. 1A in a hydrated state.

In a preferred embodiment, the hydrogel core 22 is configured to imbibe fluids, expanding from a dehydrated state (shown in FIG. 1A) to a hydrated state (FIG. 1D). In this regard, the hydrogel core 22 is preferably formulated as a mixture of hydrogel polyacrylonitrile. In particular, acrylamide and acrylonitrile (block co-polymer) are used. Alternatively, the hydrogel core 22 can be any hydrophilic acrylate derivative with a unique multi-block co-polymer structure or any other hydrogel material having the ability to deform and reform in a desired fashion in response to placement and removal of loads. Even further, a biologically safe polymer that can imbibe fluids while maintaining its structure under various stresses is acceptable. For example, the hydrogel core 22 can be formulated as a mixture of polyvinyl alcohol and water. Much like a normal nucleus, the hydrogel core 22 will initially swell from a dehydrated state as it absorbs fluid. When hydrated, the hydrogel core 22 will have a water content of 25–90 percent. The hydrogel material used for the hydrogel core 22 in the preferred embodiment is manufactured under the trade name HYPAN® by Hymedix International, Inc. of Dayton, N.J.

As shown in FIG. 1A, the hydrogel core 22 defines a leading end 28, a central portion 30 and a trailing end 32. As described in greater detail below, the leading end 28 and the trailing end 32 are in reference to a preferred orientation of the prosthetic spinal disc nucleus 20 during an implantation procedure. For the purposes of this disclosure, directional terminology such as "leading" and "trailing" are with reference to one possible orientation of the prosthetic spinal disc nucleus 20 during implantation. It should be understood, however, that due to its unique sizing, the prosthetic spinal disc nucleus 20 can be orientated in any direction relative to a nucleus cavity (not shown) or the world in general. As such, the directional terms are provided for purposes of illustration only, and should not be interpreted as limitations.

As a point of reference, the prosthetic spinal disc nucleus 20 is defined by a width (x-axis in FIGS. 1A and 1C), a length (y-axis in FIGS. 1A–1C) and a height (z-axis in FIGS. 1A and 1B). With this in mind, the hydrogel core 22, and thus the prosthetic spinal disc nucleus 20, is fabricated to assume a streamlined shape in the dehydrated state. The term "streamlined" is with reference to the hydrogel core 22 being configured, in the dehydrated state, to taper or decrease in height (z-axis) from the central portion 30 to the leading end 28, as shown most clearly in FIG. 1B (side, cross-sectional view). In one preferred embodiment, in the dehydrated state, the hydrogel core 22 is further configured to taper or decrease in height (z-axis) from the central portion 30 to the trailing end 32. With this preferred embodiment, then, opposing sides of the hydrogel core 22 are generally convex, resulting in the generally convexo-convex shape of FIG. 1B. While the taper or decrease in height (z-axis) is preferably uniform, other designs are acceptable. In general terms, a side sectional view of the hydrogel core 22 defines a leading profile 34 terminating at the leading end 28 and a trailing profile 36 terminating at the trailing end 32. The "streamlined" shape in the dehydrated state relates to the leading profile 34 being conical, tapering in height to the leading end 28. Further, in a preferred embodiment, the trailing profile 36 is also conical.

In addition to the above-described streamlined shape, in one preferred embodiment, a top, cross-sectional view (FIG. 1C) shows the central portion 30 of the hydrogel core 22 as being curved. More particularly, and with reference to FIG. 1C, opposing sides of the hydrogel core 22 curve in a generally symmetrical fashion from the leading end 28 to the trailing end 32. Alternatively, the opposing side may be linear, non-symmetrical etc.

Completely surrounding the hydrogel core 22 is the constraining jacket 24. The constraining jacket 24 is preferably a flexible tube made of tightly woven high molecular weight, high tenacity polymeric fabric. In a preferred embodiment, high molecular weight polyethylene is used as the weave material for the constraining jacket 24. However, polyester or any high tenacity polymeric material can be employed, and carbon fiber yarns, ceramic fibers, metallic fibers, etc., also are acceptable.

The constraining jacket 24 is preferably made of fibers that have been highly orientated along their length. As a result, the constraining jacket 24 material, while flexible, has little elasticity or stretch. The constraining jacket 24 defines a generally fixed maximum volume, including a generally fixed length (y-axis of FIGS. 1A–1C). In one preferred embodiment, the generally fixed maximum volume of the constraining jacket 24 is less than a theoretical volume of the hydrogel core 22 if allowed to completely hydrate without constraint. Thus, because the hydrogel core 22 has a natural, fully hydrated volume greater than the constraining jacket 24, the constraining jacket 24 will be tight about the hydrogel core 22 when hydrated, as described in greater detail below. Additionally, the volume differential between the constraining jacket 24 and the hydrated hydrogel core 22 serves to extend the useful life of the prosthetic spinal disc nucleus 20. In particular, the constraining jacket 24 effectively prevents the hydrogel core 22 from reaching its natural hydration level. Consequently, the hydrogel core 22 will have a constant affinity for imbibing additional fluid. Finally, as shown in FIGS. 1B and 1C, the hydrogel core 22 is preferably configured such that in the dehydrated state, the hydrogel core 22 has a length approximating the generally fixed maximum length of the constraining jacket 24. Thus, the hydrogel core 22 causes the constraining jacket 24 to be relatively taut along its length (y-axis). Notably, the hydrogel core 22 in the dehydrated state does not encompass the entire available volume of the constraining jacket 24.

The preferred woven construction of the constraining jacket 24 creates a plurality of small openings 38. Each of the plurality of small openings 38 is large enough to allow bodily fluids to interact with the hydrogel core 22 otherwise maintained within the constraining jacket 24. However, each of the plurality of small openings 38 is small enough to prevent the hydrogel core 22 from escaping. Each of the plurality of small openings 38 preferably has an average diameter of about 10 micrometers, although other dimensions are acceptable. In this regard, although the constraining jacket 24 has been described as having a woven configuration, any other configuration having a semi-permeable or porous attribute can be used. Finally, the constraining jacket 24 material preferably allows for tissue in-growth and is textured to provide a grip or purchase within a disc space (not shown).

As indicated above, the hydrogel core 22 is configured to expand from the dehydrated shape, shown in FIGS. 1A–1C, to a hydrated shape, shown in FIG. 1D, following implant. Manufacture of the hydrogel core 22 is described in greater detail below. Generally speaking, however, the hydrogel core 22 is constructed such that the hydrated shape is different from the dehydrated shape. In other words, the hydrogel core 22 has a streamlined shape in the dehydrated state to facilitate implant, and preferably has a shape generally corresponding to the shape of a portion of a nucleus cavity (not shown) in the hydrated state. One example of the hydrated prosthetic spinal disc nucleus 20 is shown in FIG. 1D. In the hydrated state, the hydrogel core 22, and thus the prosthetic spinal disc nucleus 20, defines an anterior face 50 (partially hidden in FIG. 1D), a posterior face 52, and opposing end plate faces 54, 56 (partially hidden in FIG. 1D). The opposing end plate faces 54, 56 may also be referred to as a superior face and an inferior face, respectively. For the purposes of this disclosure, directional terminology such as "anterior," "posterior," "superior," and "inferior" are with reference with one possible orientation of the prosthetic spinal disc nucleus 20 within a nucleus cavity (not shown). It should be understood, however, that due to its unique sizing, the prosthetic spinal disc nucleus 20 can be orientated in any direction relative to a nucleus cavity or the world in general. As such, the directional terms are provided for purposes of illustration only, and should not be interpreted as limitations. As a point of reference, FIG. 1D again identifies the leading end 28 and the trailing end 32.

A comparison of the prosthetic spinal disc nucleus 20 in the dehydrated state (FIG. 1A) with that of the hydrated state (FIG. 1D) graphically illustrates the preferred transition in shape of the hydrogel core 22. The hydrogel core 22 has transitioned, upon hydration, from the streamlined configuration of FIG. 1A to a rectangular configuration of FIG. 1D. In particular, the hydrogel core 22 in the hydrated state does not taper from the central portion 30 to the leading end 28 or the trailing end 32. Instead, the hydrogel core 22 has a relatively uniform height (z-axis in FIG. 1D). In other words, with hydration, the hydrogel core 22 transitions from the substantially convexo-convex cross-sectional shape of FIG. 1B to the rectangular (or plano-plano) shape of FIG. 1D. Further, in the hydrated state, the central portion 30 of the hydrogel core 22 is no longer curved along its length, as previously described with reference to the preferred embodiment of FIG. 1C. As described in greater detail below, the prosthetic spinal disc nucleus 20 in the hydrated state is uniquely designed to generally adhere to the spacing requirements of a particular disc space (not shown).

The desired dehydrated and hydrated shapes of the prosthetic spinal disc nucleus 20, and in particular the hydrogel core 22, are generated during manufacture. First, the hydrogel core 22 is formulated. In the preferred embodiment, the selected hydrogel material has an inherent shape memory attribute. An appropriate volume of hydrogel material, dissolved or suspended in a solvent, is poured into a mold having a shape corresponding to the desired hydrated shape. For example, to achieve the rectangular configuration of the prosthetic spinal disc nucleus 20 of FIG. 1D, the hydrogel material is poured into a mold having a rectangular shape. Once cast, a solvent exchange process is performed, replacing the solvent with water such that the hydrogel material hydrates to a maximum hydration level, thereby creating the hydrogel core 22. As a result of this solvent exchange process, a rectangular, hydrated shape is imparted into the shape memory of the hydrogel core 22.

In the hydrated state, the hydrogel core 22 is relatively soft. To aid in ensuring proper placement of the prosthetic spinal disc nucleus 20 within an intervertebral disc space and to review the stability of the prosthetic spinal disc nucleus 20 during follow-ups, a radiopaque wire (not shown) may be forced into the hydrogel core. The radiopaque wire is preferably made of a platinum-iridium material, but can be any other material having radiopaque and biologically inert characteristics. Notably, the preferred platinum-iridium material is visible by normal, inexpensive x-ray procedures, as well as by computer-generated imaging.

The hydrogel core 22 is then preferably placed in an oven and dehydrated, resulting in an under-sized, rectangular-shaped body. The hydrogel core 22, in a dehydrated state, is then inserted into the constraining jacket 24.

Prior to insertion of the hydrogel core 22, the constraining jacket 24 is an elongated, open-ended tube, and does not include the closures 26. The dehydrated hydrogel core 22 is inserted axially into the constraining jacket 24 through one of the open ends and centrally positioned. The open ends of the constraining jacket 24 are then secured by forming the closures 26. For example, the material at the open ends may be folded and then closed by sewing a dense, bar-tack stitch at a position near the hydrogel core 22. The bar-tack stitch material is preferably the same high tenacity, high polymeric material, such as a high molecular weight polyethylene, as is used for the constraining jacket 24. By employing the same material for both the constraining jacket 24 and the bar-tack stitch, the biocompatibility of the entire prosthetic spinal disc nucleus 20 is ensured. Any excess material is removed from the constraining jacket 24 by a thermal cut. This thermal cut fuses the potentially fraying ends of the constraining jacket 24 distal the stitching.

Following closure of the constraining jacket 24 about the hydrogel core 22, the prosthetic spinal disc 20, and in particular the hydrogel core 22, is rehydrated. In this regard, the hydrogel core 22 is allowed to hydrate and expand to a volumetric limit of the constraining jacket 24.

Assuming the constraining jacket 24 and the closures 26 do not fail, the hydrogel core 22 is then "conditioned". This conditioning amounts to at least three compressive loads being applied across the length of the prosthetic spinal disc nucleus 20. The selected magnitude of the compressive loads relates to an in vivo compressive load normally encountered by a patient. In this regard, the magnitude of in vivo compressive loads varies from patient to patient and is a function of a patient's size and spinal level. For example, published literature has stated that the normal standing or sitting compressive load on the discal area is 1.8 multiplied by the patient's body weight. Further, the maximum compressive load placed on the lumbar discal area during normal, daily activities is 3.6 multiplied by the patient's body weight. The conditioning, therefore, will consist of a series of compressive loads being placed on the prosthetic spinal disc nucleus 20 equivalent to a maximum of 1.8 multiplied by a typical body weight, up to a maximum of 3.6 multiplied by a typical body weight.

With reference to FIG. 1D, the compressive loads are applied along a plane substantially normal to the opposing end plate faces 54, 56. To accomplish this effect, the hydrogel core 22 is preferably maintained within a clamp configured to maintain the rectangular shape of the hydrogel core 22.

As a result of the above-described conditioning, in combination with other elements such as size, shape, etc., the hydrogel core 22, and thus the prosthetic spinal disc nucleus 20, will have a known load bearing ability. The resulting hydrogel core 22 is viscoelastic, having a defined cross-sectional area and thickness, as well as a defined compression modules of elasticity. Due to conditioning, the hydrogel core 22, and thus the prosthetic spinal disc nucleus 20, will consistently adhere to a known change in height in response to various loads. The conditioning ensures that the hydrogel core 22 is deformable, but essentially is not compressible.

Following conditioning, the hydrogel core 22 is reshaped and dehydrated. More particularly, the prosthetic spinal disc nucleus 20 is placed into a mold having a streamlined shape corresponding to the shape of the hydrogel core 22 shown in FIGS. 1A–1C. The streamlined-shaped mold is secured about the prosthetic spinal disc nucleus 20 and exerts a pressure onto the hydrogel core 22. The mold containing the prosthetic spinal disc nucleus 20 is preferably placed in an oven to expedite dehydration of the hydrogel core 22. Following this processing, the dehydrated hydrogel core 22 assumes the streamlined shape previously described. Once again, following reshaping and in the dehydrated state, the hydrogel core 22 has a length (y-axis in FIGS. 1B and 1C) approximating the generally fixed maximum length of the constraining jacket 24. Thus, the constraining jacket 24 is relatively taut along its length (y-axis in FIG. 1A–1C). Upon hydration, the hydrogel core 22 will expand to the shape shown in FIG. 1D due to the shape memory attribute of the hydrogel material.

Prior to implant, the prosthetic spinal disc nucleus 20 is preferably, but not necessarily, maintained, in a dehydrated state, within a retaining tube (not shown) sized to maintain the generally streamlined shape of the hydrogel core 22. The retaining tube is preferably made of implantable grade stainless steel, but can be any other surgically safe material such as polyethylene. The prosthetic spinal disc nucleus 20 and its retaining tube may be packaged in a dry foam. The entire surgical package is sterilized in a tray, via gas, steam or other form of sterilization. Once conditioned, reshaped and sterilized, the dehydrated prosthetic spinal disc nucleus 20 is ready for implantation into a human disc space (not shown).

Importantly, the above-described manufacturing process allows for the production of the prosthetic spinal disc nucleus having a number of different hydrated shapes. For example, as described in greater detail below, one advantage of a prosthesis of the present invention is the general conformance, upon hydration, to the anatomical shape of a general area or a compartment of a disc space. For example, the prosthetic spinal disc nucleus 20 has been shown as, in the hydrated state, generally assuming a rectangular shape. It should be understood, however, that an individual disc space or intradiscal area/compartment may present additional anatomical variations. In recognition of these anatomical variances, the prosthetic spinal disc nucleus 20 in accordance with the present invention may be manufactured to assume other shapes in the hydrated state. For example, one alternative embodiment of a prosthetic spinal disc nucleus 70 is shown in FIGS. 2A and 2B.

Figure 2A:
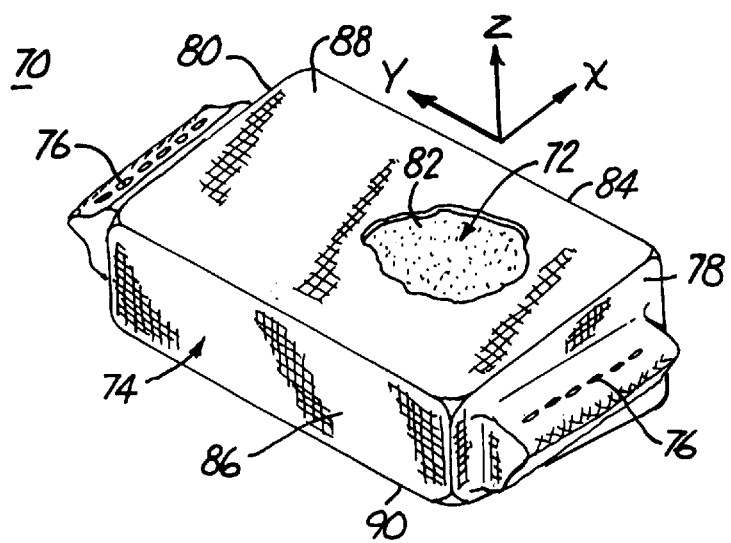
FIGS. 2A and 2B are perspective views of an alternative prosthetic spinal disc nucleus, including a cutaway view showing a portion of a hydrogel core, in accordance with the present invention.
Figure 2B:
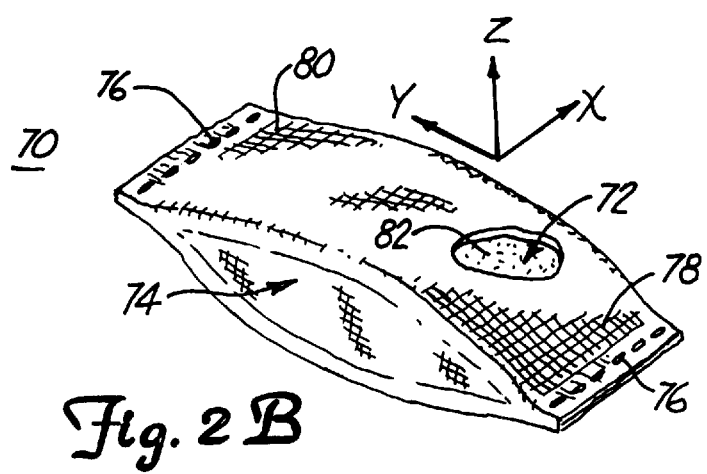

The prosthetic spinal disc nucleus 70 is shown in a hydrated state in FIG. 2A, and a dehydrated state in FIG. 2B. The prosthetic spinal disc nucleus 70 is highly similar to the prosthetic spinal disc nucleus 20 (FIG. 1A) previously described and is comprised of a hydrogel core 72 surrounded by a constraining jacket 74. The constraining jacket 74 is secured about the hydrogel core 72 by closures 76. The hydrogel core 72 has a leading end 78, trailing end 80 and central portion 82, defined most clearly in the dehydrated state (FIG. 2B). In the hydrated state (FIG. 2A), the central portion 82, and thus the prosthetic spinal disc nucleus 70, more accurately defines an anterior face 84 (shown partially in FIG. 2A), a posterior face 86, and opposing end plate faces 88, 90 (shown partially in FIG. 2A).

The prosthetic spinal disc nucleus 70 is fabricated to assume an elongated wedge shape in the hydrated state. In other words, in the hydrated state, the anterior face 84, the posterior face 86 and the opposing end plate faces 88, 90 are substantially rectangular, whereas the leading end 78 and the trailing end 80 are tapered or wedge shaped. Thus, in the hydrated state, the prosthetic spinal disc nucleus 70 has a height (z-axis in FIG. 2B) increasing from the posterior face 86 to the anterior face 84. For this reason, it should be understood that the alternative prosthetic spinal disc nucleus 70 can be referenced as a "tapered prosthetic spinal disc nucleus," whereas the prosthetic spinal disc nucleus 20 (FIGS. 1A–1D) can be referred to as a "rectangular prosthetic spinal disc nucleus."

Other than being configured to have a different shape in the hydrated state, the prosthetic spinal disc nucleus 70 is identical to the prosthetic spinal disc nucleus 20 (FIGS. 1A–1D). In a dehydrated state (FIG. 2B), the prosthetic spinal disc nucleus 70 has the same streamlined shape as the prosthetic spinal disc nucleus 20 shown in FIG. 1D. Thus, the prosthetic spinal disc nucleus 70 is manufactured in a highly similar fashion, except that a different mold is used during initial formation of the hydrogel core 72. Subsequent reshaping of the hydrogel core 72 results in the streamlined shape of FIG. 2B. Due to a shape memory attribute of the hydrogel core 72, upon hydration, the hydrogel core 72 will transition from the dehydrated, streamlined shape of FIG. 2B to the hydrated, tapered shape of FIG. 2A.

Figure 3A:
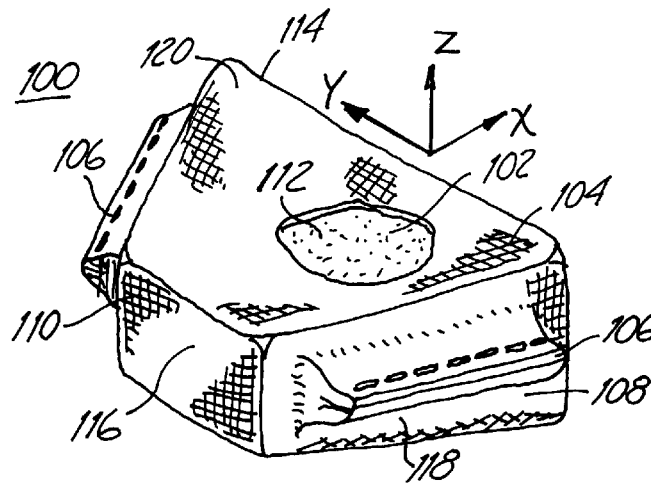
FIGS. 3A and 3B are perspective views of an alternative prosthetic spinal disc nucleus, including a cutaway view showing a portion of a hydrogel core, in accordance with the present invention.
Figure 3B:
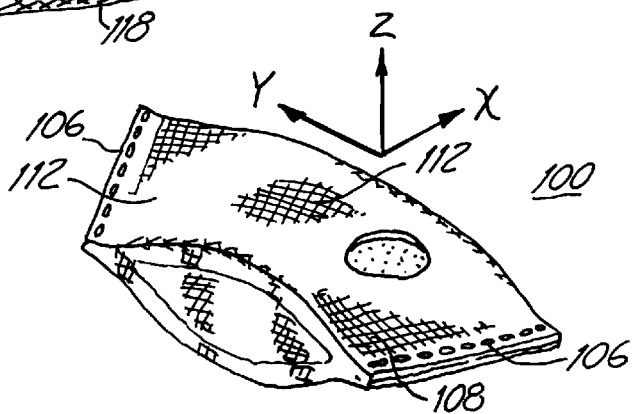

Yet another alternative embodiment of a prosthetic spinal disc nucleus 100 is shown in FIGS. 3A–3B. As a point of reference, FIG. 3A depicts the prosthetic spinal disc nucleus 100 in a hydrated state; whereas FIG. 3B is a dehydrated configuration. The prosthetic spinal disc nucleus 100 is highly similar to previous embodiments and includes a hydrogel core 102 and a constraining jacket 104. The constraining jacket 104 is secured about the hydrogel core 102 by closures 106. As seen most distinctly in the dehydrated state (FIG. 3B), the hydrogel core 102 is defined by a leading end 108, a trailing end 110 and a central portion 112. In the hydrated state (FIG. 3A), the central portion 112, and thus the prosthetic spinal disc nucleus 100, defines an anterior face 114 (partially hidden in FIG. 3A), a posterior face 116 and opposing end plate faces 118, 120 (partially hidden in FIG. 3A).

The composition and fabrication of the hydrogel core 102 and the constraining jacket 104 is virtually identical to that previously described. The actual shape of these components differs somewhat. In particular, with reference to FIG. 3A, in the hydrated state the prosthetic spinal disc nucleus 100 is configured to assume an angled, wedge shape. For this reason, the alternative prosthetic spinal disc nucleus 100 can be referred to as an "angled prosthetic spinal disc nucleus." In particular, the anterior face 114 and the posterior face 116 are substantially rectangular, the posterior face 116 being larger than the anterior face 114. Further, the leading end 108 and the trailing end 110 are wedge shaped. Finally, the opposing end plate faces 118, 120 are approximately trapezoidal or wedge-shaped. With this configuration, in the hydrated state, the angled prosthetic spinal disc nucleus 100 tapers in height (z-axis) from the posterior face 116 to the anterior face 114. The rate of change in height is preferably relatively uniform. Additionally, the angled prosthetic spinal disc nucleus 100 tapers in length (y-axis) from the posterior face 116 to the anterior face 114. In the hydrated state, then, the angled prosthetic spinal disc nucleus 100 is highly similar to the previously described tapered prosthetic spinal disc nucleus 70 (FIG. 2B), except for the generally trapezoidal shape of the opposing end plate faces 118, 120.

The preferred hydrated shape of the angled prosthetic spinal disc nucleus 100 is accomplished by, for example, use of a correspondingly shaped mold as part of the above-described manufacturing process. Similarly, the preferred dehydrated shape (FIG. 3B) of the angled prosthetic spinal disc nucleus 100 is generated by reshaping the hydrogel core 102. For example, the hydrogel core 102 may be placed in a streamlined-shaped mold and compressed while dehydrating. Regardless of the exact manufacturing technique, the resulting dehydrated angled prosthetic spinal disc nucleus 100 is preferably substantially convexo-convex, tapering in height (z-axis) from the central portion 112 to the leading end 108 and the trailing end 110. Notably, to achieve the desired hydrated shape of FIG. 3A, the hydrogel core 102 may taper in length (y-axis) in the dehydrated state such that the hydrogel core 102 of FIG. 3B differs slightly from the hydrogel core 72 of FIG. 2B, although the dehydrated hydrogel core 102 preferably renders the constraining jacket 104 relatively taut along its length. Due to a shape memory characteristic of the hydrogel core 102, upon hydration, the hydrogel core 102 will transition from the dehydrated, streamlined shape of FIG. 3B to the hydrated, angled shape of FIG. 3A.

Figure 4A:
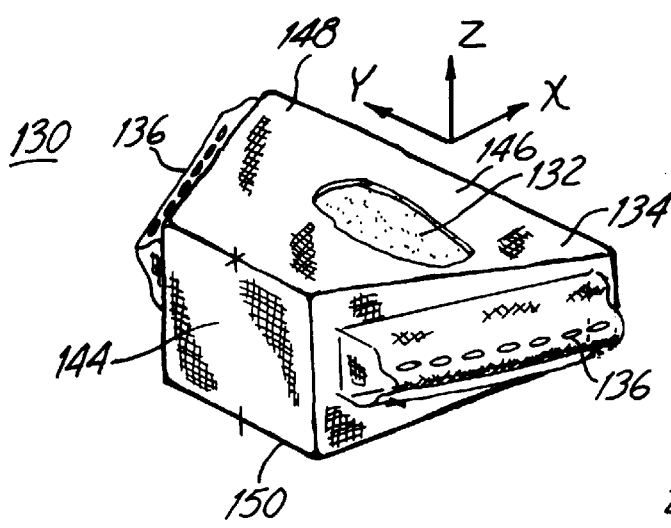
FIGS. 4A and 4B are perspective views of an alternative prosthetic spinal disc nucleus, including a cutaway view showing a portion of a hydrogel core, in accordance with the present invention.
Figure 4B:
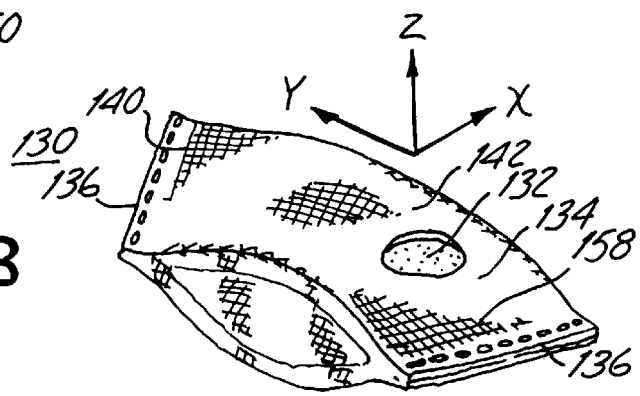
Figure 5:
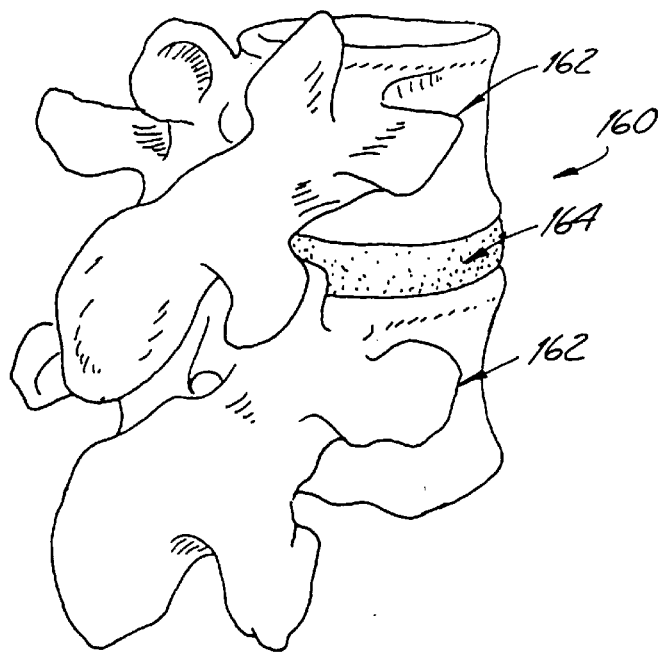
FIG. 5 is an elevated view of a spinal segment including a degenerated discal area.
Figure 6:
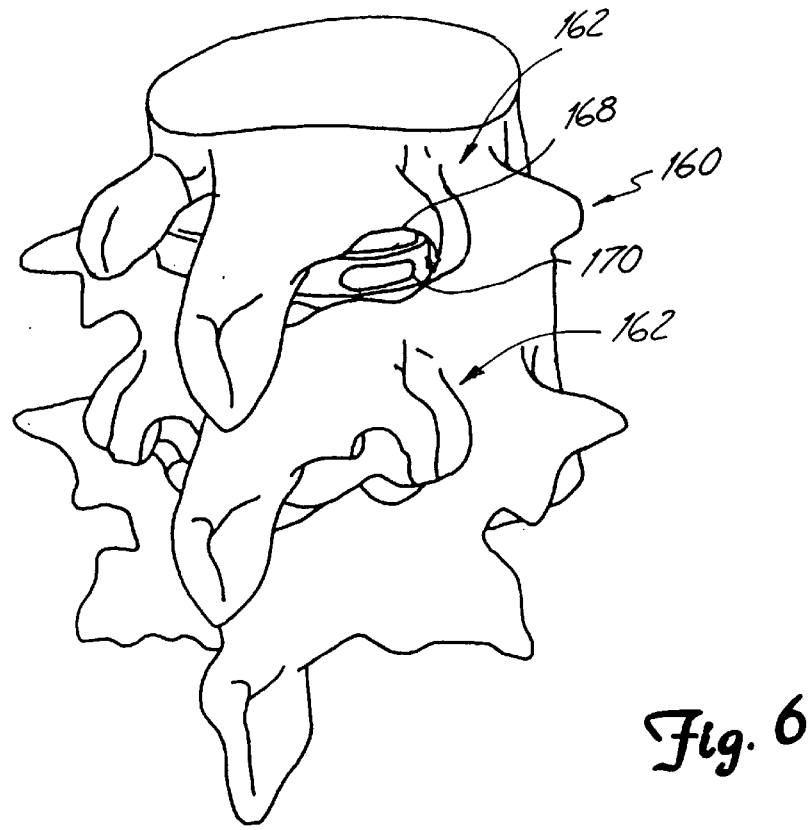
FIG. 6 is a posterior view of a portion of a human spine, showing an opening through an anulus.

Yet another alternative embodiment of a prosthetic spinal disc nucleus 130 is shown in FIGS. 4A and 4B. As a point of reference, FIG. 4A depicts the prosthetic spinal disc nucleus 130 in a hydrated state; whereas FIG. 4B is a dehydrated configuration. The alternative prosthetic spinal disc nucleus 130 is highly similar to previous embodiments and includes a hydrogel core 132 and a constraining jacket 134 secured about the hydrogel core 132 by closures 136. As depicted most distinctly in the dehydrated state (FIG. 4B), the hydrogel core 132 is defined by a leading end 138, a trailing end 140 and a central portion 142. In the hydrated state (FIG. 4A), the central portion 142, and thus the prosthetic spinal disc nucleus 130 defines an anterior face 144, a posterior face 146 (partially hidden in FIG. 4A) and opposing end plate faces 148, 150 (partially hidden in FIG. 4A).

The composition and fabrication of the hydrogel core 132 and the constraining jacket 134 is virtually identical to that previously described. The actual shape of these components upon hydration differs somewhat. In particular, with reference to FIG. 4A, in the hydrated state, the prosthetic spinal disc nucleus 130 is configured to assume an angled, wedge-shape. This shape has a reverse angular configuration when compared to the angled prosthetic spinal disc nucleus 100 (FIG. 3A). For this reason, the prosthetic spinal disc nucleus 130 can be referred to as a "reverse angle prosthetic spinal disc nucleus." The reverse angle prosthetic spinal disc nucleus 130, in the hydrated state, tapers in length (y-axis) from the posterior face 146 to the anterior face 144, preferably with a relatively uniform rate of change in length, such that the opposing end plate faces 148, 150 are approximately trapezoidal. Additionally, the reverse angle prosthetic spinal disc nucleus 130 tapers in height (z-axis) from the anterior face 144 to the posterior face 146, preferably with a relatively uniform rate of change in height, such that the leading end 138 and the trailing end 140 are approximately trapezoidal.

As with previous embodiments, the unique shape of the reverse angle prosthetic spinal disc nucleus 130 shown in FIG. 4A is achieved only upon hydration. In accordance with the above described manufacturing technique, however, in a dehydrated state, the reverse angle prosthetic spinal disc nucleus 130 assumes the streamlined shape shown in FIG. 4B. The preferred dehydrated shape of the reverse angle prosthetic spinal disc nucleus 130 is created during the above-described reshaping procedure. The resulting hydrogel core 132, in the dehydrated state, is preferably substantially convexo-convex, tapering in height (z-axis) from the central portion 142 to the leading end 138 and the trailing end 140. Similar to the angled prosthetic spinal disc nucleus 100 (FIG. 3B), the hydrogel core 132 of FIG. 4B has a slight taper in length (y-axis) in the dehydrated state, although is preferably configured to maintain the constraining jacket 134 in a taut position along its length (y-axis). Due to a shape memory characteristic of the hydrogel core 132, upon hydration, the hydrogel core 132 will transition from the dehydrated, streamlined shape of FIG. 4B to the hydrated, reverse angle shape of FIG. 4A.

As should be apparent from the above discussion, a prosthetic spinal disc nucleus in accordance with the present invention can be configured to assume a number of different shapes in a hydrated state. In the dehydrated state, however, a prosthetic spinal disc nucleus in accordance with the present invention will have the streamlined shape shown best in FIG. 1. To this end, the hydrated shape will generally correspond with the anatomical variations presented by a portion of a particular disc space. U.S. patent application Ser. No. 09/090,820, the teachings of which are incorporated herein by reference, describes the dimensional characteristics of several different prosthetic spinal disc nucleus devices in a hydrated state in greater detail. It should be understood, however, that a prosthetic spinal disc nucleus in accordance with the present invention may assume any other shape in the hydrated state, so long as a streamlined, dehydrated shape is provided.

Regardless of which embodiment of the above-described prosthetic spinal disc nucleus 20, 70, 100 or 130 is employed, the preferred method of implantation is identical. For example, FIGS. 5–9 depict implantation of a pair of prosthetic nuclei, including the tapered prosthetic spinal disc nucleus 70 (FIGS. 2A and 2B) and the angled prosthetic spinal disc nucleus 100 (FIGS. 3A and 3B) into a damaged disc space 160, for example at disc level L4/L5. The disc space 160 separates two adjacent vertebrae 162 and includes an anulus 164 and a nucleus region or cavity 166 (shown best in FIGS. 7A and 7B). Proper positioning is achieved by first performing a laminectomy in a targeted lamina area 168. A passage 170 is created through a posterior side of the anulus 164, such as by a simple incision or removal of a radial plug. If necessary, excess material is removed from the nucleus cavity 166 to create room for the prosthetic spinal disc nuclei 70, 100. Although in this example a single passage 170 is illustrated and discussed, a pair of passages may alternatively be used. Further, while a generally posterior technique has been identified, insertion through any portion of the anulus 164 is acceptable.

The tapered prosthetic spinal disc nucleus 70 (FIGS. 2A and 2B) and the angled prosthetic spinal disc nucleus 100 (FIGS. 3A and 3B) are then implanted into the nucleus cavity 166 via the passage 170. In this particular example, for reasons made clear below, the angled prosthetic spinal disc nucleus 100 will be implanted within an anterior area 172 of the disc space 160; whereas the tapered prosthetic spinal disc nucleus 70 will be implanted within a posterior area 174. With the preferred posterior implantation technique, then, the angled prosthetic spinal disc nucleus 100 is implanted first.

Figure 7A:
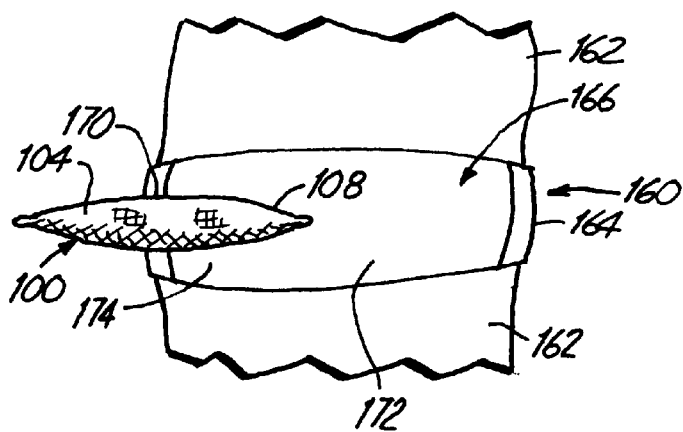
FIGS. 7A and 7B illustrate implantation of a prosthetic spinal disc nucleus into a discal segment through an opening in the anulus.
Figure 7B:
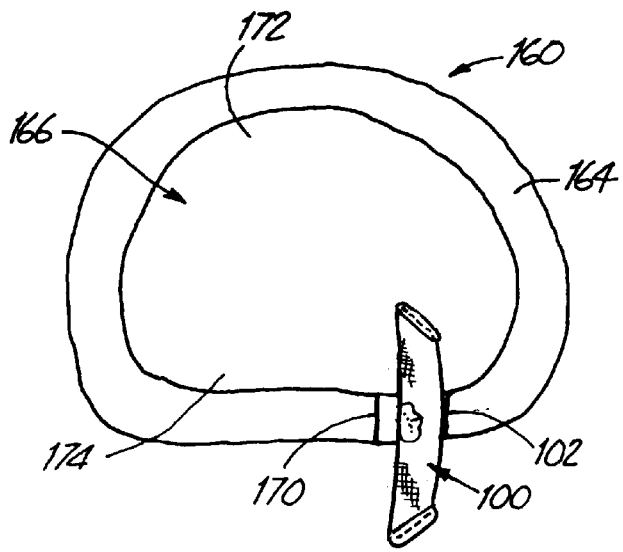
Figure 8:
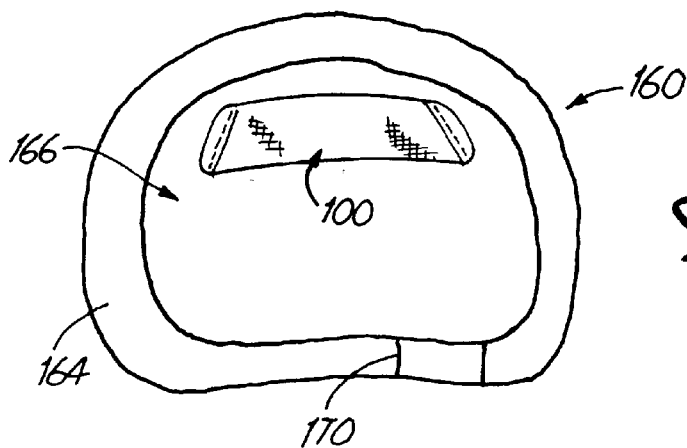
FIG. 8 is a top, sectional view of a disc space having a prosthetic spinal disc nucleus implanted in a dehydrated state.

Insertion of the angled prosthetic spinal disc nucleus 100 is shown in greater detail in FIGS. 7A and 7B. During implantation, the angled prosthetic spinal disc nucleus 100 is in a dehydrated state, thereby assuming a streamlined shape (FIG. 3B). As shown in FIG. 7A, the angled prosthetic spinal disc nucleus 100 is directed toward the anulus 164 such that the leading end 108 extends through the passage 170. As previously described, in the dehydrated state, the leading end 108 tapers in height (relative to a "height" of the nucleus cavity 166 defined by the adjacent vertebrae 162). With this tapered profile, the leading end 108 easily passes through the passage 170 of the anulus 164, thereby facilitating implantation of the angled prosthetic spinal disc nucleus 100. Because the constraining jacket 104 is relatively taut along its length (via the unique shape of the dehydrated hydrogel core 102), the constraining jacket 104 will not fold back on to itself or otherwise impede insertion through the passage 170.

Following insertion, the angled prosthetic spinal disc nucleus 100 is preferably rotated to extend transversely within the nucleus cavity 166. In this regard, as shown in FIG. 7B, where the hydrogel core 102 (in the dehydrated state) is formed to have a slight curve along its length, this transverse orientation will occur more naturally. Regardless, following rotation, the angled prosthetic spinal disc nucleus 100 is positioned within the anterior area 172 of the nucleus cavity 166. If necessary, a rod and mallet (not shown) may be used to force the angled prosthetic spinal disc nucleus 100 into the position shown in FIG. 8.

Figure 9:
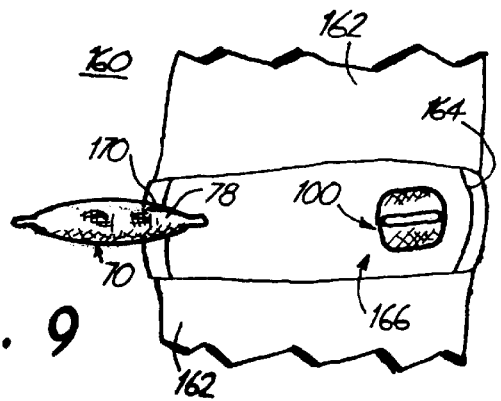
FIG. 9 is a lateral, sectional view of a disc space having one implanted prosthetic spinal disc nucleus, and a second, partially implanted prosthetic spinal disc nucleus.

The tapered prosthetic spinal disc nucleus 70 is then similarly implanted through the passage 170 in the anulus 164. As shown in FIG. 9, in a dehydrated state, the leading end 78 of the tapered prosthetic spinal disc nucleus 70 presents a tapered profile so as to facilitate insertion through the passage 170. Once inserted, the tapered prosthetic spinal disc nucleus 70 is rotated to extend transversely within the nucleus cavity 166, positioned within the posterior area 174 as shown in FIG. 10, which, for ease of illustration, depicts the nuclei 70, 100 in a hydrated state.

Notably, in certain situations, it may be desirable to slightly separate the adjacent vertebrae 162 to facilitate insertion of the prosthetic spinal disc nuclei 70, 100. With this approach, a pair of passages 170 through the anulus 164 is required. An inflatable jack, lamina spreader or similar tool (not shown) is inserted through one of the passages 170 and inflated to jack apart the adjacent vertebrae 162.: Once separation sufficient to insert the angled prosthetic spinal disc nucleus 100 is achieved, the angled prosthetic spinal disc nucleus 100 is inserted through the passage 170 otherwise not occupied by the tool. The tool is then removed, and the tapered prosthetic spinal disc nucleus 70 is placed through one of the passages 170.

The angled prosthetic spinal disc nucleus 100 is positioned such that the anterior face 114 is adjacent an anterior side of the anulus 164. The posterior face 116, conversely, is centrally located within the nucleus cavity 166. Thus, the angled prosthetic spinal disc nucleus 100 is generally positioned within the anterior area 172 of the nucleus cavity 166. The tapered prosthetic spinal disc nucleus 70 is positioned such that the posterior face 86 is adjacent a posterior side of the anulus 164, whereas the anterior face 84 is centrally located within the nucleus cavity 166. Thus, the tapered prosthetic spinal disc nucleus 70 is positioned within the posterior area 174 of the nucleus cavity 166.

Figure 10:
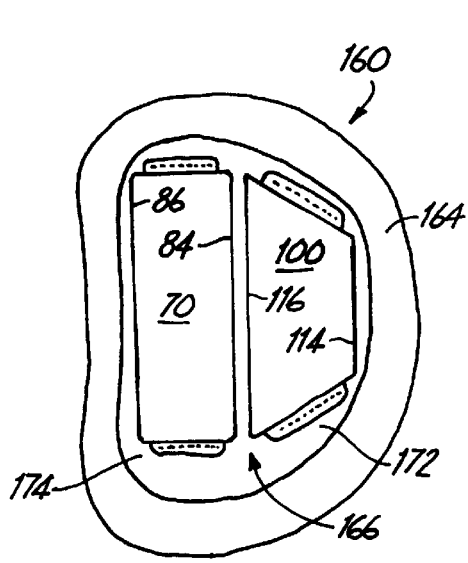
FIG. 10 is a top, sectional view of a disc space having two prosthetic spinal disc nuclei implanted and in a hydrated state.
Figure 11:
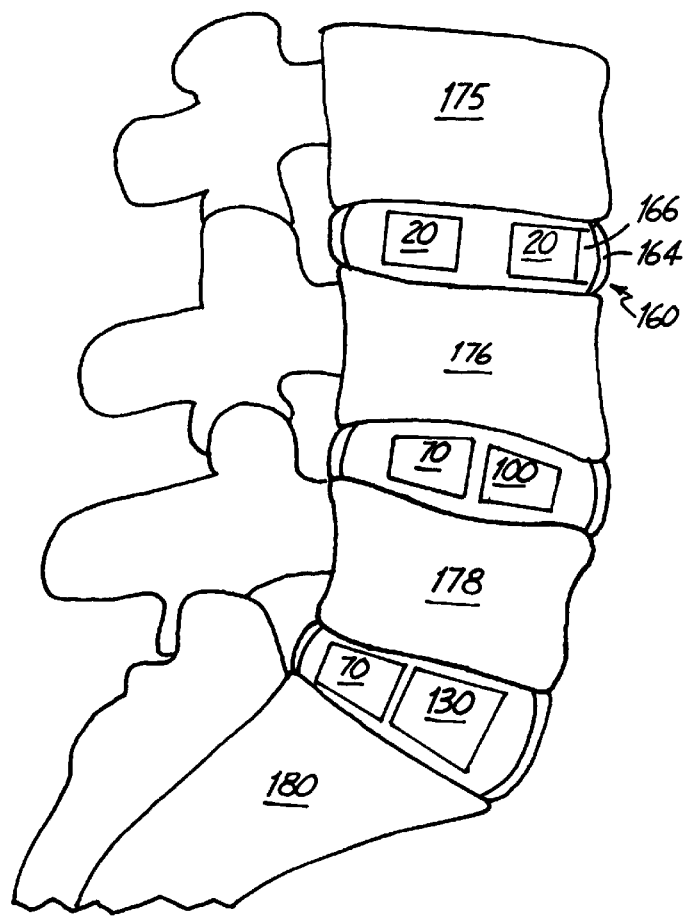
FIG. 11 is a lateral, sectional view of a human spine having several prosthetic spinal disc nuclei implanted and in a hydrated state.

As shown in FIGS. 10 and 11, upon hydration, the tapered prosthetic spinal disc nucleus 70 and the angled prosthetic spinal disc nucleus 100 are sized and orientated to generally conform to the transverse geometry of the respective areas of the nucleus cavity 166. It should be recognized, however, that orientation and selection of the prosthetic spinal disc nuclei can and will vary depending upon an individual disc space. For example, the rectangular prosthetic spinal disc nucleus 20 (FIGS. 1A–1D) and/or the reverse angle prosthetic spinal disc nucleus 130 (FIGS. 4A and 4B) may be used instead of the tapered prosthetic spinal disc nucleus 70 or the angled prosthetic spinal disc nucleus 100. Further, the particular prosthetic spinal disc nucleus 20, 70, 100, 130 employed may be rotated 180 degrees. Thus, for example, the angled prosthetic spinal disc nucleus 100 may be positioned in the posterior area 174 such that the anterior face 114 is adjacent the posterior side of the anulus 164, whereas the posterior face 116 is centrally located within the nucleus cavity 166. Simply stated, any combination, location or orientation of the prosthetic spinal disc nuclei 20, 70, 100, 130 disclosed can be used. In this regard, FIG. 11 shows the prosthetic spinal disc nuclei 20, 70, 100 and 130 in different locations and between different vertebrae, including an L-3 vertebrae 175, an L-4 vertebrae 176, an L-5 vertebrae 178 and an S-1 vertebrae 180. As should be evident from these examples, the particular prosthetic spinal disc nuclei will be selected such that in a hydrated state, the prosthesis corresponds generally to an anatomical shape of a particular side or portion of the disc space in question.

Following implantation, each of the prosthetic spinal disc nuclei 20, 70, 100 or 130 functions as an intervertebral spacer and a cushion, and potentially restores the normal fluid pumping action of the disc space 160 (FIG. 11). Function of the prosthetic nuclei is described below with reference to the rectangular prosthetic spinal disc nucleus 20 of FIGS. 1A–1D, implanted between the L-3 vertebrae 175 and the L-4 vertebrae 176 shown in FIG. 11. It should be understood, however, that the tapered prosthetic spinal disc nucleus 70, the angled prosthetic spinal disc nucleus 100 and the reverse angle prosthetic spinal disc nucleus 130 function in an identical manner. Following implant, the hydrogel core 22 imbibes fluids. In this regard, the constraining jacket 24 has sufficient flexibility to allow the hydrogel core 22 to expand. As the hydrogel core 22 hydrates, its volume increases significantly. Due to the preshaping and shape memory of the hydrogel core 22, the hydrogel core 22 will expand from the dehydrated, streamlined shape (FIG. 1A) to the hydrated, rectangular shape (FIG. 1D). Because the constraining jacket 24 is flexible, it will conform to the preferred, predetermined shape of the hydrogel core 22, as shown in FIG. 1D. At a certain, predetermined hydration point, the hydrogel core 22 reaches a horizontal expansion limit (x-y plane of FIG. 1A) of the constraining jacket 24, which becomes tight. The constraining jacket 24 has a relatively fixed maximum volume so that the constraining jacket 24 forces the hydrogel core 22 to increase mainly in height (z-axis in FIG. 1B) as more fluids are imbibed. In other words, once the hydrogel core 22 expands to the length (y-axis in FIG. 1C) and width (x-axis in FIGS. 1B and 1C) limits of the constraining jacket 24, the constraining jacket 24 forces further expansion to occur solely in height (z-axis in FIG. 1B). Thus, the constraining jacket 24 works in concert with the hydrogel core 22 to control expansion of the prosthetic spinal disc nucleus 20 after implant. With reference to the implanted position of the rectangular prosthetic spinal disc nucleus 20 shown in FIG. 11, this controlled swelling pushes apart or further separates the vertebrae 175, 176 adjacent the disc space 160, as would a normal nucleus. Importantly, the limitation on expansion of the hydrogel core 22 occurs independent of the anulus 164. In other words, the constraining jacket 24 prevents the hydrogel core 22 from expanding to a point at which it would engage and conform to an inner surface of the anulus 164. Once hydrated, the prosthetic spinal disc nucleus 20 will still have a rectangular cross-section, but may be slightly circular. The prosthetic spinal disc nucleus 20 will not expand to a completely circular cross-section due to the forces imparted by the vertebral end plates, conditioning of the hydrogel core 22 prior to implant, and the volume limits of the constraining jacket 24.

Following implant and hydration, the prosthetic spinal disc nucleus 20 will deform and reform in response to the placement and removal of loads on the disc space 160 (FIG. 11). The prosthetic spinal disc nucleus 20 flattens in response to placement of physiological loads on the spine, thus assuming a more flattened shape, and acts as a cushion against various loads placed upon it. As these loads are decreased (e.g., when the patient reclines), the hydrogel core 22 reforms back in a predetermined fashion to its original, hydrated shape, due to the conditioning process described above. To prevent the hydrogel core 22 from escaping, the constraining jacket 24 ideally has a burst strength that is greater than the swelling pressure of the hydrogel core 22 when fully hydrated.

The prosthetic spinal disc nucleus 20 also restores the natural fluid pumping action of the disc space. This relationship is best described with reference to FIG. 10, which depicts the tapered prosthetic spinal disc nucleus 70 and the angled prosthetic spinal disc nucleus 100 implanted within the nucleus cavity 166 of the disc space 160. The hydrated prosthetic spinal disc nuclei 70, 100 occupy a certain percentage, but not all of, the nucleus cavity 166. As loads upon the disc space 160 increase, the prosthetic spinal disc nuclei 70, 100 cushion the vertebral end plates (not shown) and slowly deform. As a result, the volume within the nucleus cavity 166 decreases. Notably, because the prosthetic spinal disc nuclei 70, 100 do not occupy the entire nucleus cavity 166, there is room for the prosthetic spinal disc nuclei 70, 100 to deform, and the reduction in volume of the nucleus cavity 166 is allowed to take place as would otherwise occur with a normal nucleus. In this regard, the respective hydrogel cores 72, 102 (FIGS. 2A and 3A) will flatten or deform as a whole, but not decrease in volume in response to the load so that the prosthetic spinal disc nuclei 70, 100 now occupy a larger percentage of the nucleus cavity 166. As a result of the reduction in space, fluids otherwise found within the nucleus cavity 166 are forced out of the disc space 160, thus flushing out the accumulated acids or autotoxins contained therein.

Conversely, when the load is removed or decreased, the prosthetic spinal disc nuclei 70, 100 reform back to a more circular (but wedge-shaped) cross-sectional shape. This entails an increase in the vertical direction (relative to the spine in an upright position), causing the vertebral end plates (not shown) to separate, creating an increased volume in the nucleus cavity 166. It will be remembered that the respective hydrogel cores 72, 102 (FIGS. 2A and 3A) do not increase in volume, but simply reform. As a result, bodily fluid, containing beneficial nutrients, fills the now-increased volume of the nucleus cavity 166, revitalizing the overall disc space 160. Thus, the prosthetic spinal disc nuclei 20, 70, 100 or 130 act in concert with the natural disc space 160 to restore the natural pumping action of the disc space.

Notably, the prosthetic spinal disc nucleus 20, 70, 100 or 130 of the present invention independently absorbs the force/pressure placed upon the disc space 160. Thus, the anulus 164 is not required to support the force/pressure generated by swelling of the hydrogel core 22, 72, 102 or 132 during hydration. The anulus 164 does not provide any circumferential support to the prosthetic spinal disc nucleus 20, 70, 100 or 130.

The prosthetic spinal disc nucleus of the present invention: (a) restores and maintains the height of the damaged disc space; (b) restores and tightens the natural anulus to stop further degeneration and permit its healing; (c) restores the normal load-unload cycling and thus flushes out toxic by-products, bringing in fresh nutrients to the disc space; (d) allows a near-normal range of motion; (e) relieves the movement-induced discogenic pain of the vertebral segment; and (f) allows the use of a minimal, posterior surgical procedure that provides both cost and medical benefits. In short, the prosthetic spinal disc nucleus of the present invention has the ability to elevate the disc space from the inside, as does the normal, highly hygroscopic nucleus. It will tighten the ligamentous anulus and therefore promote the health and repairability of anular fibers. Beyond these functions, the prosthetic spinal disc nucleus of the present is configured to have a pre-implant dehydrated shape that facilitates implantation. Subsequently, upon hydration, the prosthetic spinal disc nucleus of the present invention transitions to a hydrated shape corresponding generally to an anatomical shape of at least a portion of a disc space.

Although the present invention has been described with reference to preferred embodiments, workers skilled in the art will recognize that changes may be made in form and detail without departing from the spirit and scope of the invention. For example, other methods of sealing the ends of the constraining jacket exist such as heat, ultrasound, crimp ring seals or spin entanglement. Additionally, more than a single layer of material may be used to maintain the integrity of the hydrogel core. In other words, a plurality of jackets can surround the hydrogel core. With respect to implantation of the prosthesis of the present invention, it has been preferably described that the prosthetic spinal disc nucleus be implanted without the assistance of implant tools. Alternatively, however, the shape change characteristic can be used to facilitate insertion via a tubed projection device, such as a cannula. By imparting a streamlined pre-implant shape into the prosthesis, the prosthesis will easily pass through a cannula into the disc space.

The hydrogel itself can have an outer "skin" formed by ion implantation which causes outer layer cross linking and functions as the constraining jacket or as an interposed membrane between the gel mass and the constraining jacket. Alternatively, expansion and contraction of the hydrogel core can be achieved via the use of a hydrogel that readily expels fluid. Further, other means exist for limiting expansion and contraction in height of the hydrogel core without the use of a separate jacket.

What is claimed is:

1. A prosthetic spinal disc nucleus for implantation into a nucleus cavity of a spinal disc, the nucleus cavity having a height defined by an opposing pair of vertebrae and an outer periphery defined by an anulus, the prosthetic spinal disc nucleus comprising:
 a formed hydrogel core configured to expand from a dehydrated state to a hydrated state, the hydrogel core being configured to have a dehydrated shape in the dehydrated state that facilitates insertion of the prosthetic spinal disc nucleus through an opening in the anulus and being generally different from a hydrated shape of the hydrogel core in the hydrated state; and
 a constraining jacket surrounding the hydrogel core, the constraining jacket being flexible but substantially inelastic.

2. The prosthetic spinal disc nucleus of claim 1, wherein the constraining jacket has a generally fixed maximum volume that is less than the volume of the nucleus cavity.

3. The prosthetic spinal disc nucleus of claim 1, wherein the dehydrated shape is streamlined.

4. The prosthetic spinal disc nucleus of claim 1, wherein the dehydrated shape is substantially convexo-convex in transverse cross-section, whereas the hydrated shape is substantially plano-plano.

5. The prosthetic spinal disc nucleus of claim 1, wherein the hydrogel core is defined by a leading end, a central portion, a trailing end and a height corresponding generally with a height of the nucleus cavity, and further wherein the dehydrated shape tapers in height from the central portion to the leading end for insertion of the leading end through the opening in the anulus.

6. The prosthetic spinal disc nucleus of claim 5, wherein the leading end and the central portion of the hydrated shape have a relatively uniform height.

7. The prosthetic spinal disc nucleus of claim 5, wherein the dehydrated shape includes a leading profile terminating at the leading end, the leading profile being generally conical.

8. The prosthetic spinal disc nucleus of claim 5, wherein the dehydrated shape tapers in height from the central portion to the trailing end for insertion of the trailing end through the opening in the anulus.

9. The prosthetic spinal disc nucleus of claim 1, wherein the hydrogel core is elongated and is defined by a leading end, a central portion, a trailing end and a length corresponding generally with a transverse width of the nucleus cavity as defined by the anulus, and further wherein the central portion of the dehydrated shape is curved to facilitate a transverse orientation of the prosthetic spinal disc nucleus in the nucleus cavity upon passage through the opening in the anulus.

10. The prosthetic spinal disc nucleus of claim 9, wherein the central portion of the hydrated shape is generally linear.

11. The prosthetic spinal disc nucleus of claim 1, wherein the constraining jacket has a generally fixed length, and further wherein the dehydrated shape of the hydrogel core has a length approximating the generally fixed length of the constraining jacket.

12. A method of manufacturing a prosthetic spinal disc nucleus for implantation into a nucleus cavity of a spinal disc, the nucleus cavity defined by an opposing pair of vertebral bodies and an anulus, the method including:

providing a hydrogel material that expands from a dehydrated state to a hydrated state;

forming a hydrogel core from the hydrogel material, the hydrogel core being formed to have a first shape in the hydrated state;

inserting the hydrogel core into a constraining jacket; and reshaping the hydrogel core to have a second shape in the dehydrated state, the second shape being different from the first shape, and wherein the hydrogel core will transition from the second shape to the first shape upon hydration.

13. The method of claim 12, wherein the hydrogel material has a shape memory attribute, and further wherein forming the hydrogel core includes:

imparting the first shape into the shape memory of the hydrogel core.

14. The method of claim 12, wherein reshaping the hydrogel core includes:

dehydrating the hydrogel core.

15. The method of claim 12, wherein reshaping the hydrogel core to have a second shape in the dehydrated state includes:

forcing the hydrogel core to an elongated shape defined by a leading end, a trailing end and a central portion, the second shape of the hydrogel core tapering from the central portion to the leading end.

16. The method of claim 15, wherein reshaping the hydrogel core to have a second shape further includes:

forming the second shape of the hydrogel core such that a leading profile of the hydrogel core is generally conical.

17. The method of claim 15, wherein reshaping the hydrogel core to have a second shape further includes:

forming the second shape of the hydrogel core such that the central portion is curved.

18. The method of claim 12, wherein the constraining jacket is substantially inelastic, having a generally fixed maximum length, and further wherein reshaping the hydrogel core to have a second shape includes:

forming the second shape of the hydrogel core to have a length approximating the generally fixed maximum length of the constraining jacket.

19. The method of claim 12, wherein forming a hydrogel core from the hydrogel material includes:

pouring the hydrogel material, in a liquid state, into a mold having a shape corresponding with the first shape.

20. A prosthetic spinal disc nucleus for implantation into a nucleus cavity of a spinal disc, the nucleus cavity having a height defined by an opposing pair of end plates and an outer periphery defined by an anulus, the prosthetic spinal disc nucleus comprising:

a formed hydrogel core configured to expand from a dehydrated state to a hydrated state, the hydrogel core having a streamlined shape in the dehydrated state and a wedge shape in the hydrated state, the hydrogel core being configured to transition from the streamlined shape to the wedge shape upon hydration; and a constraining jacket surrounding the hydrogel core, the constraining jacket being flexible but substantially inelastic and having a generally fixed maximum volume that is less than a volume of the nucleus cavity.

* * * * *